United States Patent
Kaushik et al.

(10) Patent No.: US 10,556,872 B2
(45) Date of Patent: Feb. 11, 2020

(54) FATTY ACID SYNTHASE INHIBITORS AND METHODS OF USE

(71) Applicant: Hampton University, Hampton, VA (US)

(72) Inventors: Vivek Kaushik, Newport News, VA (US); Anandkrishnan Iyer, Yorktown, VA (US); Neelam Azad, Yorktown, VA (US)

(73) Assignee: Hampton University, Hampton, VA (US)

( * ) Notice: Subject to any disclaimer, the term of this patent is extended or adjusted under 35 U.S.C. 154(b) by 0 days.

(21) Appl. No.: 15/924,886

(22) Filed: Mar. 19, 2018

(65) Prior Publication Data

US 2018/0265479 A1 Sep. 20, 2018

Related U.S. Application Data

(60) Provisional application No. 62/472,882, filed on Mar. 17, 2017.

(51) Int. Cl.
  *C07D 239/553* (2006.01)
  *A61P 35/00* (2006.01)
  *A61K 47/69* (2017.01)

(52) U.S. Cl.
  CPC ...... *C07D 239/553* (2013.01); *A61K 47/6911* (2017.08); *A61P 35/00* (2018.01)

(58) Field of Classification Search
  CPC .................................................. C07D 239/553
  See application file for complete search history.

(56) References Cited

U.S. PATENT DOCUMENTS

| | | |
|---|---|---|
| 2002/0042392 A1 | 4/2002 | Spector et al. |
| 2009/0286755 A1 | 11/2009 | Fukushima |

OTHER PUBLICATIONS

Zhou, et al. Document No. 156:477642, retrieved from STN; 2012.*
Zu, et al. Document No. 140:259645, retrieved from STN; (2004).*
Mochizuki, et al. Document No. 134:266007, retrieved from STN; (2001).*
Qiu, et al., 'Discovery of Uracil Derivatives as Potent Inhibitors of Fatty Acid Amide Hydrolase', Molecules, Feb. 18, 2016, vol. 21, pp. 1-11.
Mochizuki, et al., 'Crystal Structure of Long Alkyl 3-(Thymin-1-yl)propionates: Style of Hydrogen Bonding and Dependence on the Alkyl Chain Length', Bulletin of the Chemical Society of Japan, Jul. 1, 2002, vol. 74, pp. 193-200.
International Search Report and Written Opinion issued in International Patent Application No. PCT/US2018/023147, dated Aug. 1, 2018.

* cited by examiner

*Primary Examiner* — Shawquia Jackson
(74) *Attorney, Agent, or Firm* — Leason Ellis LLP

(57) ABSTRACT

The present disclosure provides for methods of treating cancer in a subject. In certain embodiments, the method comprises administering a therapeutically effective amount of an inhibitor of fatty acid synthase, or a pharmaceutically acceptable salt or prodrug thereof.

7 Claims, 4 Drawing Sheets

FATTY ACID SYNTHASE INHIBITORS AND METHODS OF USE

CROSS REFERENCE TO RELATED APPLICATION

This application claims priority to U.S. Provisional Application No. 62/472,882 filed on Mar. 17, 2017, which is incorporated herein by reference in its entirety.

TECHNICAL FIELD

The present disclosure relates to a class of fatty acid synthase inhibitors, and more particularly, to palmitate-based fatty acid synthase inhibitors, the pharmaceutical compositions comprising the fatty acid synthase inhibitors, and the administration of the fatty acid synthase inhibitors for the treatment of cancer.

BACKGROUND

Fatty acid synthase (FAS or FASN) is an enzyme that catalyzes the synthesis of fatty acids. Its primary function is the de novo synthesis of palmitate from acetyl coenzyme A (acetyl-CoA) and malonyl coenzyme A (malonyl-CoA). In most normal human cells, FAS may be minimally expressed. However, in some cancers (e.g., breast cancer, prostate cancer, and lung cancer), FAS may be upregulated, and this overexpression may be associated with poor prognosis. The upregulation of FAS in cancer cells makes FAS a desirable target for chemotherapeutic inhibition and cancer therapy.

Cerulenin (IUPAC name: (2R,3S)-3-[(4E,7E)-nona-4,7-dienoyl]oxirane-2-carboxamide) was identified as a naturally occurring FAS inhibitor. However, cerulenin is chemically unstable, and its use as a therapeutic is generally limited because of this instability. ORLISTAT® (tetrahydrolipstatin; IUPAC name: (S)-((S)-1-((2S,3S)-3-Hexyl-4-oxooxetan-2-yl)tridecan-2-yl) 2-formamido-4-methylpentanoate), Hoffman-La Roche, N.J.), is used in the treatment of obesity. However, ORLISTAT® has not been extensively studied as a cancer chemotherapeutic, and ORLISTAT® may also possess cellular off-targets which may make it undesirable as a cancer chemotherapeutic. Other FAS inhibitors include triclosan, osthole, C75 (4-methylene-2-octyl-5-oxotetra-hydrofuran-3-carboxylic acid), and epigallocatechin-3-gallate (EGCG).

There is a need to identify and study novel FAS inhibitors.

SUMMARY

The present disclosure provides for a compound of Formula (I), as illustrated below:

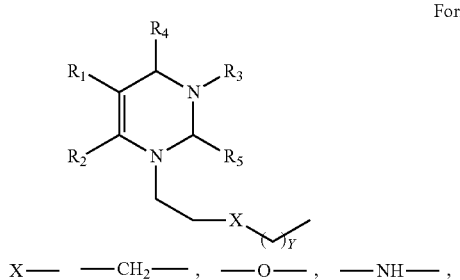

Formula (I)

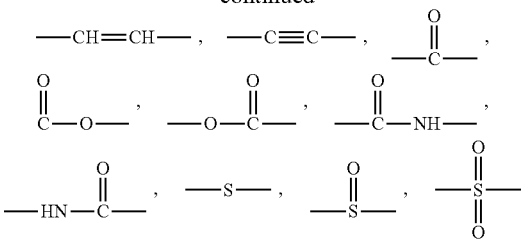

or a pharmaceutically acceptable salt thereof, wherein each $R_1$, $R_2$ and $R_3$ group is independently selected from hydrogen, alkyl, alkenyl, alkynyl, aromatic, heterocyclic, halogen, hydroxyl, carbonyl, aldehyde, carboxylic acid, ester, ether, amide, amino, nitro, nitrile, thiol, sulfonic acid, and the like; wherein each $R_4$ and $R_5$ group is independently selected from carbonyl, hydroxyl, and the like; wherein the X group is independently selected from alkyl, alkenyl, alkynyl, amine, ether, carbonyl, ester, carboxamide, sulfide, sulfinyl, sulfonyl, and the like. Any of the carbonyl groups may interconvert to hydroxyl groups and vice versa, for example, as tautomeric isomers. Y (the length of the carbon chain) may be between 2 and 20 (the carbon chain may be between 2 and 20 carbons), The carbon chain may be saturated or unsaturated.

$R_1$ may be bromine. X may be an ester. Y may be 15. $R_3$ may be hydrogen. Either $R_4$ or $R_5$ may be a hydroxyl. Either $R_1$ or $R_2$ may be a halogen.

Specific embodiment relates to the compounds of Formula (II)-(V) as illustrated below:

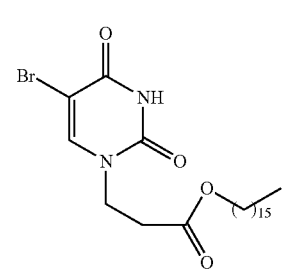

Formula (II)

Formula (III)

Formula (IV)

-continued

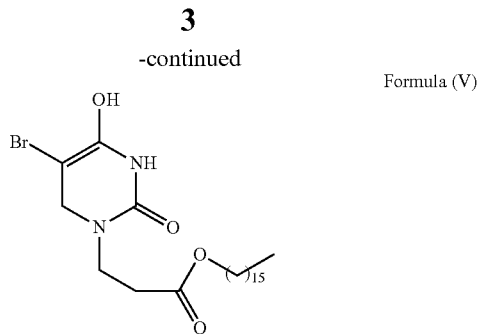

Formula (V)

Isomeric forms of the illustrated formulae may also be used in any of the examples or embodiments discussed herein.

The embodiments also relate to pharmaceutical compositions comprising a compound of Formula (I), Formula (II), Formula (III), Formula (IV), and/or Formula (V), or a pharmaceutically acceptable salt thereof, with a pharmaceutically acceptable carrier. In one embodiment, the pharmaceutically acceptable carrier is a liposome.

The embodiments also relate to methods of treating cancer where the method comprises administering an effective amount of a compound of Formula (I), Formula (II), Formula (III), Formula (IV), and/or Formula (V), or a pharmaceutically acceptable salt thereof, to a subject with cancer.

The present method may further comprise administering a second compound to the subject, where the second compound is different from the compound of Formula (I), Formula (II), Formula (III), Formula (IV), and/or Formula (V), or a pharmaceutically acceptable salt thereof. For example, the second compound may be a chemotherapeutic agent.

The present method may further comprise administering radiation to the subject.

The cancer may be a breast cancer, prostate cancer, lung cancer, or combinations thereof.

In certain embodiments, the effective amount of the present compound ranges from about 0.1 mg/kg to about 100 mg/kg body weight of the subject.

BRIEF DESCRIPTION OF THE DRAWINGS

Illustrative examples of the present disclosure are described in detail below with reference to the attached figures, which are incorporated by reference herein.

ACC: acetyl-CoA carboxylase; pACC: phosphorylated ACC; AMPKα: adenosine monophosphate-activated protein kinase; pAMPKα: phosphorylated AMPKα. β-actin was used as a control.

Figure 4:
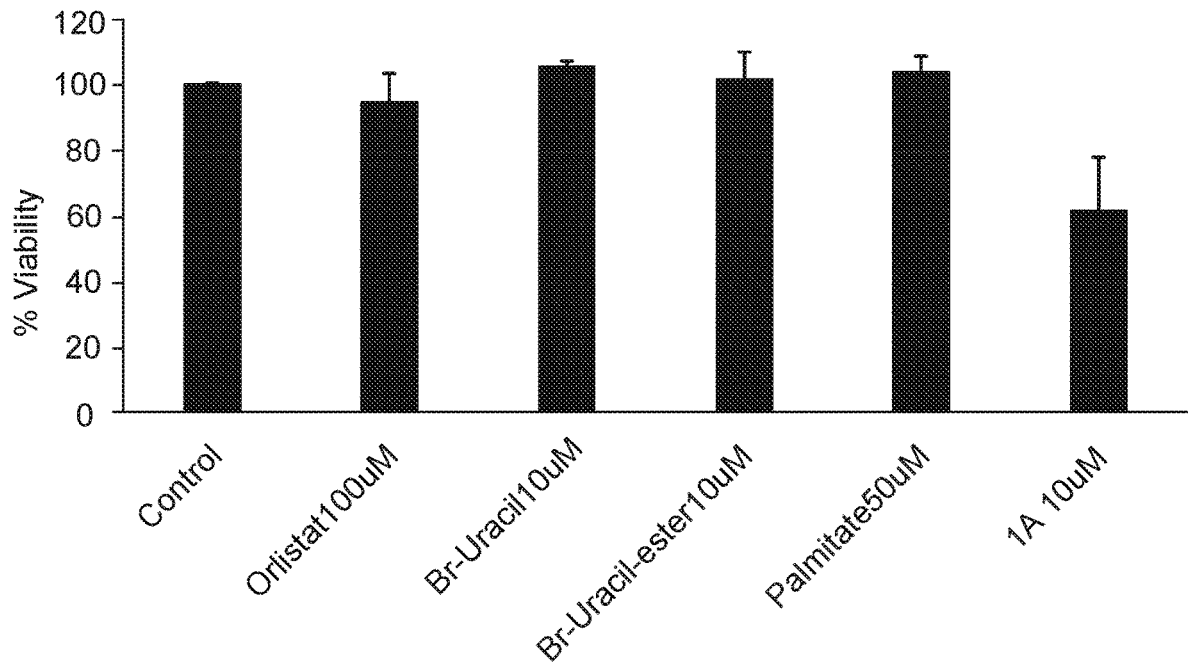

FIG. 4 illustrates MTT assay results showing cell viability for H460 lung cancer cells treated with the FAS inhibitor, Compound 1A, at the concentration of 10 μM, for 24 hours.

Figure 5:
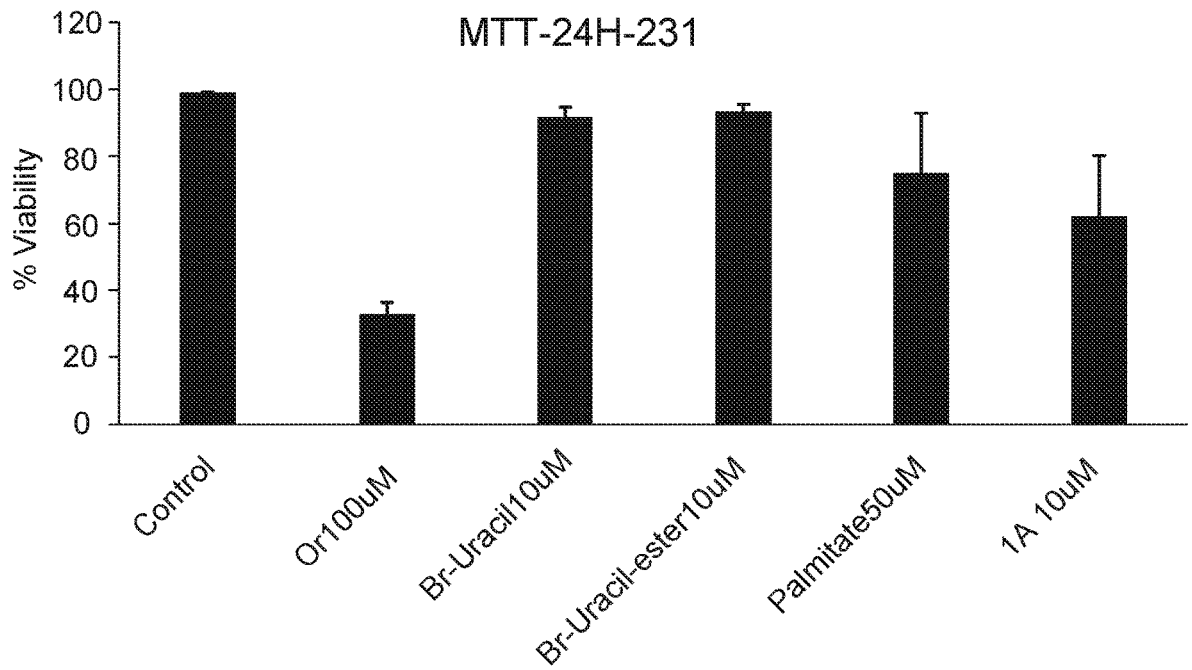

FIG. 5 illustrates MTT assay results showing cell viability for MDA-MB-231 breast cancer cells treated with the FAS inhibitor, Compound 1A, at the concentration of 10 μM, for 24 hours.

Figure 6A:
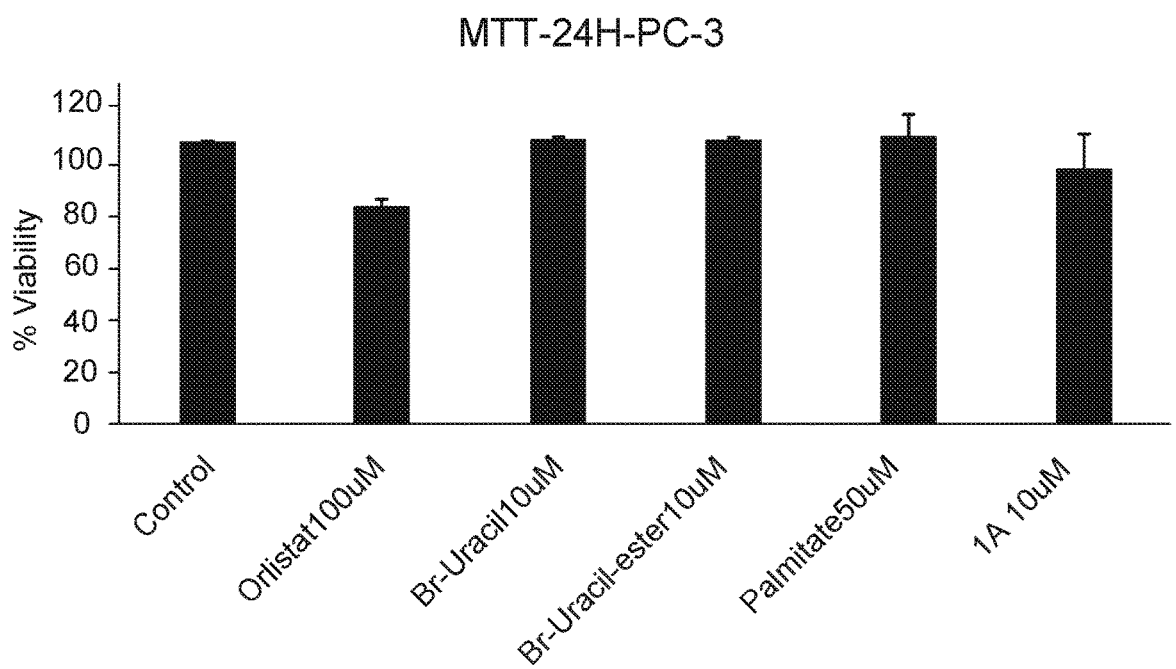
Figure 6B:
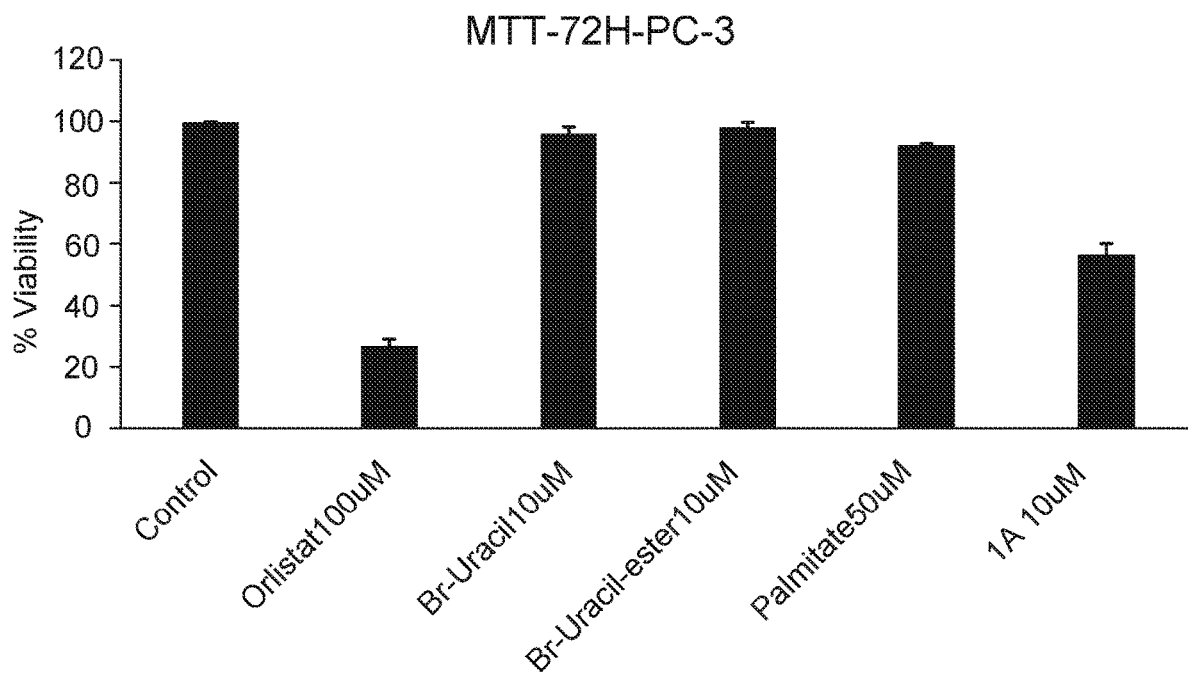

FIGS. 6A-6B illustrate MTT assay results showing cell viability for PC-3 prostate cancer cells treated with the FAS inhibitor, Compound 1A, at the concentration of 10 μM, for 24 hours (FIG. 6A) or 72 hours (FIG. 6B).

The illustrated figures are exemplary only and are not intended to assert or imply any limitation with regard to the environment, architecture, design, or process in which different examples may be implemented.

DETAILED DESCRIPTION

The present disclosure relates to a class of fatty acid synthase inhibitors, and more particularly, to palmitate-based fatty acid synthase inhibitors, pharmaceutical compositions comprising the palmitate-based fatty acid synthase inhibitors. The present fatty acid synthase inhibitors may be used for the treatment, prophylaxis or alleviation of cancer or related conditions (e.g., amelioration of signs and/or symptoms of cancer).

The present compound may inhibit fatty acid synthase through any mechanism, including, but not limited to, inhibiting/reducing fatty acid synthase activity, inhibiting/reducing fatty acid synthase level, and/or inhibiting/reducing fatty acid synthase gene expression.

The present disclosure also provides for a method of treating, or treating prophylactically, a disease such as cancer in a subject, the method comprising the step of delivering to the subject an effective amount (e.g., a therapeutically effective amount) of the present fatty acid synthase inhibitor. The inhibitor may be a compound having the formula according to Formula (I), Formula (II), Formula (III), Formula (IV), or Formula (V).

The present compound/composition can be administered alone, or may be co-administered together with radiation or another agent (e.g., a chemotherapeutic agent), to treat a disease such as cancer. Treatments may be sequential, with the present compound/composition being administered before or after the administration of other agents. For example, the present compound/composition may be used to sensitize a cancer patient to radiation or chemotherapy. Alternatively, agents may be administered concurrently.

The route of administration may vary, and can include, inhalation, intranasal, oral, transdermal, intravenous, subcutaneous or intramuscular injection.

Fatty Acid Synthase (FAS) Inhibitors

The present disclosure provides for a class of FAS inhibitors (or inhibiting compounds). The FAS inhibitor comprises a tethering group and a carbon chain as illustrated below:

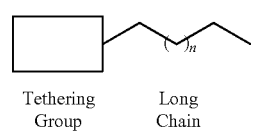

Tethering Group      Long Chain

The present disclosure provides for a general embodiment relating to the compound of Formula (I) as illustrated below:

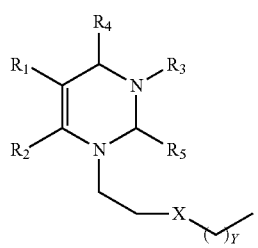

Formula (I)

wherein each $R_1$, $R_2$ and $R_3$ group is independently selected from hydrogen, alkyl, alkenyl, alkynyl, aromatic, heterocyclic, halogen, hydroxyl, carbonyl, aldehyde, carboxylic acid, ester, ether, amide, amino, nitro, nitrile, thiol, sulfonic acid, and the like; wherein each $R_4$ and $R_5$ group is independently selected from carbonyl, hydroxyl, and the like; wherein the X group is independently selected from alkyl, alkenyl, alkynyl, amine, ether, carbonyl, ester, carboxamide, sulfide, sulfinyl, sulfonyl, and the like. Any of the carbonyl groups may interconvert to hydroxyl groups and vice versa, for example, as tautomeric isomers. The length of the carbon chain Y may be between 2 and 20 carbons, between 3 and 19 carbons, between 4 and 18 carbons, between 5 and 18 carbons, between 6 and 18 carbons, between 7 and 18 carbons, between 8 and 18 carbons, between 9 and 18 carbons, between 10 and 18 carbons, between 11 and 18 carbons, between 10 and 17 carbons, between 10 and 16 carbons, between 12 and 18 carbons, between 12 and 16 carbons, between 13 and 16 carbons, between about 12 and 15 carbons, about 2, about 3, about 4, about 5, about 6, about 7, about 8, about 9, about 10, about 11, about 12, about 13, about 14, about 15, about 16, about 17, about 18, about 19, or about 20, carbons. In other words, Y may be between 2 and 20, between 3 and 19, between 4 and 18, between 5 and 18, between 6 and 18, between 7 and 18, between 8 and 18, between 9 and 18, between 10 and 18, between 11 and 18, between 10 and 17, between 10 and 16, between 12 and 18, between 12 and 16, between 13 and 16, between 12 and 15, about 2, about 3, about 4, about 5, about 6, about 7, about 8, about 9, about 10, about 11, about 12, about 13, about 14, about 15, about 16, about 17, about 18, about 19, or about 20. The carbon chain may be saturated or unsaturated. The carbon chain may be linear or branched.

The present disclosure provides for a specific embodiment relating to the compound of Formula (II) as illustrated below:

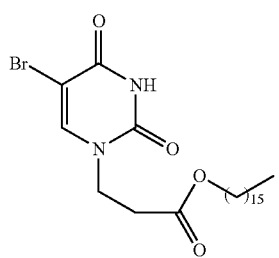

Formula (II)

The present disclosure provides for a specific embodiment relating to the compound of Formula (III) as illustrated below:

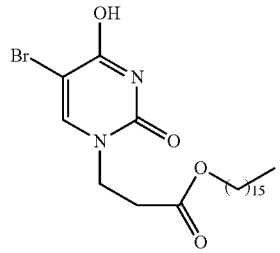

Formula (III)

The present disclosure provides for a specific embodiment relating to the compound of Formula (IV) as illustrated below:

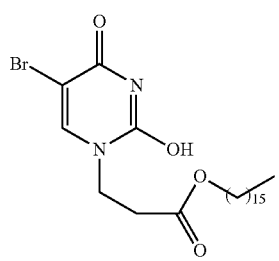

Formula (IV)

The present disclosure provides for a specific embodiment relating to the compound of the Formula (V) as illustrated below:

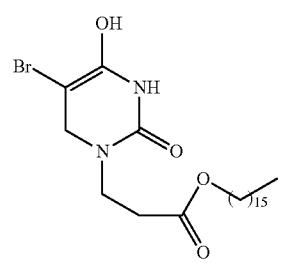

Formula (V)

Isomeric forms of the specific formulae illustrated above are also included in the present disclosure.

An exemplary FAS inhibiting compound may be synthesized by the following scheme:

Scheme I

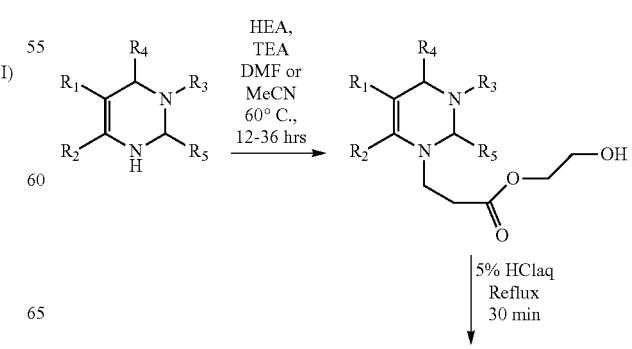

-continued

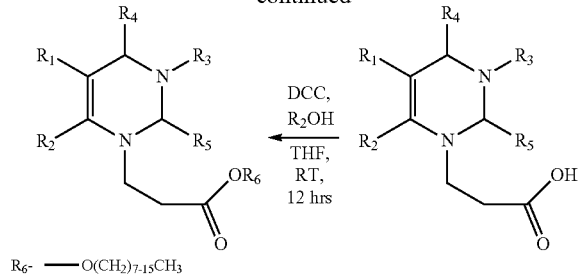

R$_6$- ——O(CH$_2$)$_{7-15}$CH$_3$

The compounds of the instant invention may be in a salt form. As used herein, a "salt" is a salt of the instant compounds which has been modified by making acid, or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates/nitrites, esters, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate/nitrite, ester, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J". Pharm. Sci. 66:1-19). The compounds may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

The salts of the present disclosure may be pharmaceutically acceptable salts. Salts encompassed within the term "pharmaceutically acceptable salts" may refer to non-toxic salts of the disclosed FAS inhibiting compounds (inhibitors). Salts of the FAS inhibiting compounds may comprise acid addition salts. In general, the salts are formed from pharmaceutically acceptable inorganic and organic acids. More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, triethiodide, and valerate salts.

Other salts, which may not be pharmaceutically acceptable, may be useful in the preparation of compounds of this disclosure, and should be considered to form a further aspect of the embodiments. These salts, such as oxalic or trifluoroacetate, while not in themselves may not be pharmaceutically acceptable, may be useful in the preparation of salts useful as intermediates in obtaining the disclosed FAS inhibiting compounds and their pharmaceutically acceptable salts.

The compounds of the present disclosure include all hydrates, solvates, and complexes of the compounds disclosed herein. If a chiral center or another form of an isomeric center is present in a compound of the present disclosure, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present disclosure may be in racemic form or as individual enantiomers. The enantiomers may be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases where compounds may exist in tautomeric forms, such as keto-enol tautomers, each tautomeric form is contemplated as being included within this invention whether existing in equilibrium or predominantly in one form.

As used herein, the term "solvate" refers to a complex of variable stoichiometry formed by a solute (in this invention, a compound of Formula I, Formula II, Formula III, Formula IV, or Formula V, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid.

As used herein, the term "prodrug" refers to a compound (e.g., a drug precursor) that is transformed in vivo to yield a compound of Formula I, Formula II, Formula III, Formula IV, or Formula V, or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

When the structure of the compounds includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, N Y, 1981. For example, the resolution may be carried out by preparative chromatography on a chiral column.

The FAS inhibiting compounds of Formula (I) or a salt thereof may exist in stereoisomeric forms (e.g., it contains one or more asymmetric carbon atoms). The individual stereoisomers (enantiomers and diastereomers) and mixtures of these are included within the scope of the present disclosure. Also contemplated by the present disclosure is that the individual isomers of the FAS inhibiting compound or salt represented by Formula (I) may be mixtures with isomers thereof in which one or more chiral centers are inverted. Likewise, it is to be understood that a FAS inhibiting compound or salt of Formula (I) may exist in tautomeric forms other than that shown in the formula and these are also included within the scope of the present disclosure. It is to be understood that the present disclosure includes all combinations and subsets of the particular groups defined hereinabove. The scope of the present disclosure includes mixtures of stereoisomers as well as purified enantiomers or enantiomerically/diastereomerically enriched mixtures. Also included within the scope of the present disclosure are individual isomers of the FAS inhibiting compound represented by Formula (I), as well as any wholly or partially equilibrated mixtures thereof. The present disclosure also includes the individual isomers of the FAS inhibiting compound or salt represented by the Formula (I) as well as mixtures with isomers thereof in which one or more chiral centers are inverted. It is to be understood that the present disclosure includes all combinations and subsets of the particular groups defined hereinabove.

The present disclosure also includes the use of all isotopes of atoms occurring on the compounds disclosed herein. Isotopes include those atoms having the same atomic number but different mass numbers. Any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein. Any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein. Isotopically-labeled compounds can generally be prepared by conventional techniques known to those skilled in the art or by processes analogous to those described in the Examples disclosed herein using appropriate isotopically-labeled reagents in place of the non-labeled reagents employed.

In certain embodiments, the present compound has an IC50 in inhibiting fatty acid synthase activity ranging from about 0.1 µM to about 500 µM, from about 0.5 µM to about 200 µM, from about 1 µM to about 100 µM, from about 1 µM to about 50 µM, from about 1 µM to about 30 µM, from about 1 µM to about 10 µM, from about 5 µM to about 15 µM, from about 10 µM to about 20 µM, about 5 µM, or about 10 µM. In certain embodiments, the present compound displays at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, or at least 50 fold, efficacy to inhibit fatty acid synthase activity in vitro and in vivo compared to tetrahydrolipstatin (or ORLISTAT®).

As used herein, "alkyl" includes both branched and straight-chain saturated aliphatic hydrocarbon groups having the specified number of carbon atoms and may be unsubstituted or substituted. In one embodiment, the alkyls are C1-C10 alkyls, or a subset or individual thereof. In a non-limiting example, where the alkyl is C1-C5 as in "C1-C5 alkyl", it is defined to include groups having 1, 2, 3, 4 or 5 carbons in a linear or branched arrangement and specifically includes methyl, ethyl, n-propyl, isopropyl, n-butyl, t-butyl, and pentyl. Alkyl may optionally be substituted with phenyl or substituted phenyl to provide substituted or unsubstituted benzyl.

As used herein the term "aryl" refers to aromatic monocyclic or multicyclic groups containing from 5 to 15 carbon atoms. Aryl groups include, but are not limited to, groups such as unsubstituted or substituted phenyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment. Aryl may optionally be substituted with a heterocyclyl-C(O)— moiety which includes a pyrrolidinyl-C(O)— moiety.

Heterocyclyl means a saturated or partially unsaturated monocyclic radical containing 3 to 8 ring atoms and preferably 5 to 6 ring atoms selected from carbon or nitrogen but not limited to pyrrolidine.

The term "heteroaryl" as used herein, represents a stable monocyclic, bicyclic or polycyclic ring of up to 10 atoms in each ring, wherein at least one ring is aromatic and contains from 1 to 4 heteroatoms or particularly 1 to 2 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom. selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyriinidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

In the compounds of the present invention, the alkyl, aryl, or heteroaryl groups can be further substituted by replacing one or more hydrogen atoms be alternative non-hydrogen groups. These include, but are not limited to, 1-4 groups selected from alkyl, alkoxy, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon (s) or hydrogen (s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; heterocyclyl-C(O)-moiety; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

It is understood that substituents and substitution patterns on the present compounds can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. Moreover, where hydrogens are not shown in the carbon-based structures herein, implicit hydrogens are understood to complete valences as required.

Where a numerical range is provided herein for any parameter, it is understood that all numerical subsets of that numerical range, and all the individual integer values contained therein, are provided as part of the invention. Thus, C1-C10 alkyl includes the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 10 carbon atom, etc.

Also encompassed by the present disclosure is a pharmaceutical composition comprising the present compound, e.g., a compound of Formula I, Formula II, Formula III, Formula IV, or Formula V, or a pharmaceutically acceptable salt (crystal and/or amorphous), a physiologically functional derivative, non-salt amorphous form, solvate, polymorph, tautomer or prodrug thereof. In certain embodiments, the composition further comprises a pharmaceutically acceptable carrier, diluent, excipient and/or adjuvant.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, Formula II, Formula III, Formula IV, or Formula V, and at least one pharmaceutically acceptable carrier/excipient.

The present compound may be formulated into a pharmaceutical composition, where the present compound is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), or from about 0.1% (w/w) to about 20% (w/w).

In various embodiments, the present disclosure provides methods to reduce cancer cell growth, proliferation, and/or metastasis, as measured according to routine techniques in the diagnostic art. Specific examples of relevant responses include reduced size, mass, or volume of a tumor, or reduction in cancer cell number.

The present compound/composition and methods can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; preventing, inhibiting or ameliorating the cancer in the subject, such as slowing progression of the cancer, reducing or ameliorating a sign or symptom of the cancer; reducing the rate of tumor growth in a patient; preventing the continued growth of a tumor, reducing the size of a tumor; and/or disappearance of markers associated with undesirable, unwanted, or aberrant cell proliferation. U.S. Patent Publication No. 20080275057 (incorporated herein by reference in its entirety).

Cell specific reduction of fatty acid synthase levels and/or activity may be achieved by targeted administration, i.e., applying the treatment only to the targeted cells and not other cells. However, in other embodiments, down-regulation of fatty acid synthase levels and/or activity in other cells (e.g., a portion of non-diseased cells, and not substantially in other cell or tissue types) is employed.

The methods and compositions described here may reduce the level and/or activity of fatty acid synthase, fatty acid synthase polynucleotides, and fatty acid synthase nucleic acids, as well as variants, homologues, derivatives and fragments of any of these. The terms "fatty acid synthase polynucleotide", "fatty acid synthase nucleotide" and "fatty acid synthase nucleic acid," may be used interchangeably, and should be understood to specifically include both cDNA and genomic sequences encoding fatty acid synthase. These terms are also intended to include a nucleic acid sequence capable of encoding a fatty acid synthase polypeptide and/or a fragment, derivative, homologue or variant of this.

By "inhibition", "down-regulation" or "reduction" is meant any negative effect on the condition being studied; this may be total or partial. Thus, where the level or activity of a protein (e.g., fatty acid synthase) is being detected, the present compound/composition is capable of reducing, ameliorating, or abolishing the level or activity of the protein (e.g., fatty acid synthase). The inhibition or down-regulation of the level or activity of the protein achieved by the present agent may be at least 10%, such as at least 20%, at least 30%, at least 40%, at least 50%, at least 60%, at least 70%, at least 80%, at least 90% or more compared to the level or activity of the protein (e.g., fatty acid synthase) in the absence of the present compound/composition.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the examples of the present invention. At the very least, and not as an attempt to limit the application of the doctrine of equivalents to the scope of the claim, each numerical parameter should at least be construed in light of the number of reported significant digits and by applying ordinary rounding techniques. It should be noted that when "about" is at the beginning of a numerical list, "about" modifies each number of the numerical list. Further, in some numerical listings of ranges some lower limits listed may be greater than some upper limits listed. One skilled in the art will recognize that the selected subset will require the selection of an upper limit in excess of the selected lower limit. The term "about" in reference to a numeric value refers to +10% of the stated numeric value. In other words, the numeric value can be in a range of 90% of the stated value to 110% of the stated value.

Combination Therapy

The present compound/composition may be administered alone, or in combination with a second agent/treatment method (therapeutic intervention, or a second therapeutic agent). Therapeutic interventions that may be used in combination with the present compound/composition or method can include, radiation, pharmacologic intervention, devices, surgical intervention, or any combination thereof. Pharmacologic interventions may include, but are not limited to, treatment with chemotherapeutic agents.

For example, the present compositions may be administered in combination with radiation, surgery or one or more chemotherapeutic agents (which are different from the present compound). The present compositions may be administered before, during or after the administration of radiation, surgery or chemotherapeutic agents.

The present compound/composition may also be administered in combination with antiviral agents, anti-inflammatory agents or antibiotics. The agents may be administered concurrently or sequentially. The present compound/composition can be administered before, during or after the administration of the other active agent(s).

The present compound/composition may be used in combination with radiation therapy. In one embodiment, the present invention provides for a method of treating tumor cells, such as breast cancer cells, lung cancer cells, and/or prostate cancer cells, with radiation, where the cells are treated with an effective amount of the present compound/composition, and then exposed to radiation. The present compound/composition treatment may be administered to a subject before, during, and/or after radiation.

The present compound/composition may be used in combination with chemotherapy, where the cells are treated with an effective amount of the present compound/composition, and then exposed to chemotherapy. The present compound/composition treatment may be administered to a subject before, during, and/or after chemotherapy.

Also encompassed by the present disclosure is admixtures and/or coformulations of the present compound and at least one other therapeutic agent (which is different from the present compound).

Combination therapy may be achieved by administering a pharmaceutical composition that includes both agents (the present compound and a second therapeutic agent), or by administering two pharmaceutical compositions, at the same time or within a short time period, wherein one composition comprises the present compound, and the other composition includes a second therapeutic agent.

In certain embodiments, the combination of the present compound and a second therapeutic agent produces an additive or synergistic effect (i.e., greater than additive effect) in treating the cancer compared to the effect of the present compound or the second therapeutic agent alone. For example, the combination may result in a synergistic increase in apoptosis of cancer cells, and/or a synergistic reduction in tumor volume. In different embodiments, depending on the combination and the effective amounts used, the combination of compounds can inhibit tumor growth, achieve tumor stasis, achieve substantial or complete tumor regression, and/or achieve any of the effects described herein.

The amount of the present compound or the amount of the second therapeutic agent that may be used in the combination therapy may be a therapeutically effective amount, a sub-therapeutically effective amount or a synergistically effective amount.

In one embodiment, combination therapy provides greater efficacy at the same doses, lower side effects, and/or prevents or delays the build-up of multi-drug resistance.

The present compound/composition and the second therapeutic agent or radiation may be administered simultaneously, separately or sequentially. They may exert an advantageously combined effect (e.g., additive or synergistic effects).

For sequential administration, either the present compound/composition is administered first and then the second therapeutic agent or radiation, or the second therapeutic agent or radiation is administered first and then the present compound/composition. In embodiments where the present compound/composition and the second therapeutic agent or radiation are administered separately, administration of a first agent can precede administration of a second agent by seconds, minutes, hours, days, or weeks. The time difference in non-simultaneous administrations may be greater than 1 minute, and can be, for example, precisely, at least, up to, or less than 5 minutes, 10 minutes, 15 minutes, 30 minutes, 45 minutes, 60 minutes, 2 hours, 3 hours, 6 hours, 9 hours, 12 hours, 24 hours, 36 hours, or 48 hours, or more than 48 hours. The two or more agents can be administered within minutes of each other or within about 0.5, about 1, about 2, about 3, about 4, about 6, about 9, about 12, about 15, about 18, about 24, or about 36 hours of each other or within about 1, 2, 3, 4, 5, 6, 7, 8, 9, 10, 12, 14 days of each other or within about 2, 3, 4, 5, 6, 7, 8, 9, or 10 weeks of each other. In some cases, longer intervals are possible.

The present disclosure also provides for a pharmaceutical composition comprising (i) the present compound; (ii) the second therapeutic agent; and (iii) at least one pharmaceutically acceptable excipient.

Chemotherapeutic Agents for Combination Therapy

Chemotherapeutic agents that may be used in combination with the present compound/composition include, but are not limited to, alkylating agents, anti-metabolites, anti-microtubule agents, topoisomerase inhibitors, cytotoxic antibiotics, endoplasmic reticulum stress inducing agents, platinum compounds, vincalkaloids, taxanes, epothilones, enzyme inhibitors, receptor antagonists, tyrosine kinase inhibitors, boron radiosensitizers (i.e. velcade), and chemotherapeutic combination therapies.

Non-limiting examples of DNA alkylating agents are nitrogen mustards, such as Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, Triaziquone, Triethylenemelamine; Hydrazines (Procarbazine); Triazenes such as Dacarbazine and Temozolomide (TMZ); Altretamine and Mitobronitol.

Non-limiting examples of Topoisomerase I inhibitors include Campothecin derivatives including SN-38, APC, NPC, campothecin, topotecan, exatecan mesylate, 9-nitro-camptothecin, 9-aminocamptothecin, lurtotecan, rubitecan, silatecan, gimatecan, diflomotecan, extatecan, BN-80927, DX-8951f, and MAG-CPT as decribed in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(24):7107-7116 and Gatto et al. (1996) *Cancer Res.* 15(12):2795-2800; Phenanthroline derivatives including Benzo[i]phenanthridine, Nitidine, and fagaronine as described in Makhey et al. (2003) *Bioorg. Med. Chem.* 11 (8): 1809-1820; Terbenzimidazole and derivatives thereof as described in Xu (1998) *Biochemistry* 37(10):3558-3566; and Anthracycline derivatives including Doxorubicin, Daunorubicin, and Mitoxantrone as described in Foglesong et al. (1992) *Cancer Chemother. Pharmacol.* 30(2):123-125, Crow et al. (1994) *J. Med. Chem.* 37(19):31913194, and Crespi et al. (1986) *Biochem. Biophys. Res. Commun.* 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]pyrimidines, and Anthracenyl-amino Acid Conjugates as described in Denny and Baguley (2003) *Curr. Top. Med. Chem.* 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compounds are a subclass of DNA alkylating agents. Non-limiting examples of such agents include Cisplatin, Nedaplatin, Oxaliplatin, Triplatin tetranitrate, Satraplatin, Aroplatin, Lobaplatin, and JM-216. (See McKeage et al. (1997) *J. Clin. Oncol.* 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Non-limiting examples of antimetabolite agents include folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4-dihydroxypyridine and potassium oxonate), ralitirexed (tomudex), nolatrexed (Thymitaq, AG337), LY231514 and ZD9331, as described for example in Papamicheal (1999) The Oncologist 4:478-487.

In an embodiment, the purines discussed herein are one or more of adenosine, inosine, hypoxanthine, or adenine.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (e.g., Tipifarnib); CDK inhibitors (e.g., Alvocidib, Seliciclib); proteasome inhibitors (e.g., Bortezomib); phosphodiesterase inhibitors (e.g., Anagrelide; rolipram); IMP dehydrogenase inhibitors (e.g., Tiazofurine); and lipoxygenase inhibitors (e.g., Masoprocol).

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

Chemotherapeutic agents may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

Conditions to be Treated

Cancers treated using methods and compositions described herein are characterized by abnormal cell proliferation including, but not limited to, pre-neoplastic hyperproliferation, cancer in-situ, neoplasms and metastasis.

Cancers that can be treated by the present compositions and methods include, but are not limited to, breast cancer, lung cancer, prostate cancer, colorectal cancer, melanoma, pancreatic cancer, cervical cancer, thyroid cancer, bladder cancer, non-small cell lung cancer, liver cancer, prostate cancer, muscle cancer, hematological malignancies, endometrial cancer, lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, ovarian cancer, gastric cancer, esophageal cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, ear, nose and throat cancer, hematopoietic cancer, biliary tract cancer; bladder cancer; bone cancer; choriocarcinoma; connective tissue cancer; cancer of the digestive system; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; lymphoma including Hodgkin's and Non-Hodgkin's lymphoma; myeloma; fibroma, oral cavity cancer (e.g., lip, tongue, mouth, and pharynx); prostate cancer; retinoblastoma; rhabdomyosarcoma; rectal cancer; renal cancer; cancer of the respiratory system; skin cancer; stomach cancer; testicular cancer; uterine cancer; cancer of the urinary system, as well as other carcinomas and sarcomas. U.S. Pat. No. 7,601,355.

The present compound/composition may be used alone or in combination with other chemotherapeutic agents via topical application for the treatment of localized cancers such as breast cancer or melanomas.

The present disclosure also provides a method for inhibiting the growth of a cell in vitro, ex vivo or in vivo, where a cell, such as a cancer cell, is contacted with an effective amount of the present compound/composition.

Pathological cells or tissue such as hyperproliferative cells or tissue may be treated by contacting the cells or tissue with an effective amount of the present compound/composition. The cells, such as cancer cells, can be primary cancer cells or can be cultured cells available from tissue banks such as the American Type Culture Collection (ATCC). The pathological cells can be cells of lung cancer, prostate cancer, breast cancer, a systemic cancer, gliomas, meningiomas, pituitary adenomas, or a CNS metastasis from a systemic cancer, hematopoietic cancer or ovarian cancer. The cells can be from a vertebrate, preferably a mammal, more preferably a human.

In vitro efficacy (e.g., cytotoxicity effects) of the present compound/composition can be determined using methods well known in the art. For example, the cytoxicity of the present compound/composition may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65: 55 63, 1983. The cytoxicity of the present compound/composition may be studied by colony formation assay. Functional assays for inhibition of VEGF secretion and IL-8 secretion may be performed via ELISA. Cell cycle block by the compound/composition may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

Cytotoxicity effects of the present compound/composition can also be determined by other suitable assay, including, but not limited to, assessing cell membrane integrity (using, e.g., dyes such as trypan blue or propidium iodide, or using lactate dehydrogenase (LDH) assay), measuring enzyme activity, measuring cell adherence, measuring ATP production, measuring co-enzyme production, measuring nucleotide uptake activity, crystal violet method, Tritium-labeled Thymidine uptake method, measuring lactate dehydrogenase (LDH) activity, MTS (3-(4,5-dimethylthiazol-2-yl)-5-(3-carboxymethoxyphenyl)-2-(4-sulfophenyl)-2H-tetrazolium) assay, sulforhodamine B (SRB) assay, WST (watersoluble tetrazolium salts) assay, clonogenic assay, cell number count, monitoring cell growth, etc.

Apoptosis of cells may be assayed by any suitable method, including, but not limited to, TUNEL (terminal deoxynucleotidyl transferase dUTP nick end labeling) assay, assaying levels of cytochrome C release, assaying levels of cleaved/activated caspases, assaying 5-bromo-2'-deoxyuridine labeled fragmented DNA, assaying levels of survivin etc.

Other methods that can be used to show the effects of the present methods, pharmaceutical compositions include, but are not limited to, clonogenic assay (colony formation assay) to show decrease in cell survival and/or proliferation, studying tumor volume reduction in animal models (such as in mice, etc.)

Pharmaceutical Compositions

The present disclosure provides for a pharmaceutical composition comprising the present compound.

The present compound may be present in the pharmaceutical composition in an amount ranging from about 0.005% (w/w) to about 100% (w/w), from about 0.01% (w/w) to about 90% (w/w), from about 0.1% (w/w) to about 80% (w/w), from about 1% (w/w) to about 70% (w/w), from about 10% (w/w) to about 60% (w/w), from about 0.01% (w/w) to about 15% (w/w), or from about 0.1% (w/w) to about 20% (w/w).

To prepare such pharmaceutical compositions, one or more of compound of the present disclosure may be mixed with a pharmaceutical acceptable excipient, e.g., a carrier, adjuvant and/or diluent, according to conventional pharmaceutical compounding techniques.

Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers, preservatives and adjuvants, see Remington's Pharmaceutical Sciences, edited by E. W. Martin (Mack Publishing Company, 18th ed., 1990). Additional excipients, for example sweetening, flavoring and coloring agents, may also be present.

The pharmaceutically acceptable carrier/excipient may be selected from the group consisting of fillers, e.g. sugars and/or sugar alcohols, e.g. lactose, sorbitol, mannitol, maltodextrin, etc.; surfactants, e.g. sodium lauryle sulfate, Brij 96 or Tween 80; disintegrants, e.g. sodium starch glycolate, maize starch or derivatives thereof; binder, e.g. povidone, crosspovidone, polyvinylalcohols, hydroxypropylmethylcellulose; lubricants, e.g. stearic acid or its salts; flowability enhancers, e.g. silicium dioxide; sweeteners, e.g. aspartame; and/or colorants. Pharmaceutically acceptable carriers include any and all clinically useful solvents, dispersion media, coatings, antibacterial and antifungal agents, isotonic and absorption delaying agents and the like.

The pharmaceutical composition may contain excipients for modifying, maintaining or preserving, for example, the pH, osmolarity, viscosity, clarity, color, isotonicity, odor, sterility, stability, rate of dissolution or release, adsorption or penetration of the composition. Suitable excipients include, but are not limited to, amino acids (such as glycine, glutamine, asparagine, arginine or lysine); antimicrobials; antioxidants (such as ascorbic acid, sodium sulfite or sodium hydrogen sulfite); buffers (such as borate, bicarbonate, Tris HCl, citrates, phosphates, other organic acids); bulking agents (such as mannitol or glycine), chelating agents (such as ethylenediamine tetraacetic acid (EDTA), ethylene glycol tetraacetic acid (EGTA)); complexing agents (such as caffeine, polyvinylpyrrolidone, beta cyclodextrin or hydroxypropyl beta cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (in one aspect, sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The present compounds or pharmaceutical compositions may be administered by any route, including, without limitation, oral, transdermal, ocular, intranasal, intraperitoneal, inhalation, intravenous, ICV, intracisternal injection or infusion, subcutaneous, implant, sublingual, subcutaneous, intramuscular, intravenous, rectal, mucosal, ophthalmic, intrathecal, intra-articular, intra-arterial, sub-arachinoid, bronchial and lymphatic administration. The present composition may be administered parenterally or systemically.

The present pharmaceutical compositions can be, e.g., in a solid, semi-solid, or liquid formulation. Intranasal formulation can be delivered as a spray or in a drop; inhalation formulation can be delivered using a nebulizer or similar device; topical formulation may be in the form of gel, ointment, paste, lotion, cream, poultice, cataplasm, plaster, dermal patch aerosol, etc.; transdermal formulation may be administered via a transdermal patch or iontorphoresis. Compositions can also take the form of tablets, pills, capsules, semisolids, powders, sustained release formulations, solutions, emulsions, suspensions, elixirs, aerosols, chewing bars or any other appropriate compositions.

The composition may be administered locally via implantation of a membrane, sponge, or another appropriate material onto which the desired molecule has been absorbed or encapsulated. Where an implantation device is used, the device may be implanted into any suitable tissue or organ, and delivery of the desired molecule may be via diffusion, timed release bolus, or continuous administration.

This disclosure also provides the compositions as described above for ocular administration. As such, the compositions can further comprise a permeation enhancer. For ocular administration, the compositions described herein can be formulated as a solution, emulsion, suspension, etc.

A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

Oral dosage forms may be tablets, capsules, bars, sachets, granules, syrups and aqueous or oily suspensions. Tablets may be formed form a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound, may be prepared by known methods. The contents of the capsule may be formulated using known methods so as to give sustained release of the active compounds. Other dosage forms for oral administration include, for example, aqueous suspensions containing the active compounds in an aqueous medium in the presence of a non-toxic suspending agent such as sodium carboxymethylcellulose, and oily suspensions containing the active compounds in a suitable vegetable oil, for example *arachis* oil. The active compounds may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium. U.S. Pat. No. 8,263,662.

Intravenous forms include, but are not limited to, bolus and drip injections. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate.

Additional compositions include formulations in sustained or controlled delivery, such as using liposome or micelle carriers, bioerodible microparticles or porous beads and depot injections.

The present compound(s) or composition may be administered as a single dose, or as two or more doses (which may or may not contain the same amount of the desired molecule) over time, or as a continuous infusion via implantation device or catheter. The pharmaceutical composition can be prepared in single unit dosage forms.

Appropriate frequency of administration can be determined by one of skill in the art and can be administered once or several times per day (e.g., twice, three, four or five times daily). The compositions of the invention may also be administered once each day or once every other day. The compositions may also be given twice weekly, weekly, monthly, or semi-annually. In the case of acute administration, treatment is typically carried out for periods of hours or days, while chronic treatment can be carried out for weeks, months, or even years. U.S. Pat. No. 8,501,686.

Administration of the present compositions can be carried out using any of several standard methods including, but not limited to, continuous infusion, bolus injection, intermittent infusion, inhalation, or combinations of these methods. For example, one mode of administration that can be used involves continuous intravenous infusion. The infusion of the compositions of the invention can, if desired, be preceded by a bolus injection.

Methods of determining the most effective means and dosage of administration can vary with the composition used for therapy, the purpose of the therapy, the target cell being treated, and the subject being treated. Single or multiple administrations can be carried out with the dose level and pattern being selected by the treating physician. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

For example, the present compound may be administered to a subject at about 0.0001 mg/kg to about 500 mg/kg, about 0.01 mg/kg to about 200 mg/kg, about 0.01 mg/kg to about 0.1 mg/kg, about 0.1 mg/kg to about 100 mg/kg, about 10 mg/kg to about 200 mg/kg, about 10 mg/kg to about 20 mg/kg, about 5 mg/kg to about 15 mg/kg, about 0.0001 mg/kg to about 0.001 mg/kg, about 0.001 mg/kg to about 0.01 mg/kg, about 0.01 mg/kg to about 0.1 mg/kg, about 0.1 mg/kg to about 0.5 mg/kg, about 0.5 mg/kg to about 1 mg/kg, about 1 mg/kg to about 2.5 mg/kg, about 2.5 mg/kg to about 10 mg/kg, about 10 mg/kg to about 50 mg/kg, about 50 mg/kg to about 100 mg/kg, about 100 mg/kg to about 250 mg/kg, about 0.1 µg/kg to about 800 µg/kg, about 0.5 µg/kg to about 500 µg/kg, about 1 µg/kg to about 20 µg/kg, about 1 µg/kg to about 10 µg/kg, about 10 µg/kg to about 20 µg/kg, about 20 µg/kg to about 40 µg/kg, about 40 µg/kg to about 60 µg/kg, about 60 µg/kg to about 100 µg/kg, about 100 µg/kg to about 200 µg/kg, about 200 µg/kg to about 300 µg/kg, or about 400 µg/kg to about 600 µg/kg body weight of the subject. In some embodiments, the dose is within the range of about 250 mg/kg to about 500 mg/kg, about 0.5 mg/kg to about 50 mg/kg, or any other suitable amounts, body weight of the subject.

The effective amount of the present compound for the combination therapy may be less than, equal to, or greater than, when the compound is used alone.

The amount or dose of the present compound may range from about 0.01 mg to about 10 g, from about 0.1 mg to about 9 g, from about 1 mg to about 8 g, from about 1 mg to about 7 g, from about 5 mg to about 6 g, from about 10 mg to about 5 g, from about 20 mg to about 1 g, from about 50 mg to about 800 mg, from about 100 mg to about 500 mg, from about 600 mg to about 800 mg, from about 800 mg to about 1 g, from about 0.01 mg to about 10 g, from about 0.05 µg to about 1.5 mg, from about 10 µg to about 1 mg protein, from about 0.1 mg to about 10 mg, from about 2 mg to about 5 mg, from about 1 mg to about 20 mg, from about 30 µg to about 500 µg, from about 40 µg to about 300 µg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg.

Different dosage regimens may be used. In some embodiments, a daily dosage, such as any of the exemplary dosages described above, is administered once, twice, three times, or four times a day for at least three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer)

may be employed along with a low dosage. In some embodiments, a once- or twice-daily dosage is administered every other day.

Some embodiments provide a pharmaceutical composition (also referred to as pharmaceutical formulation) comprising a compound of Formula (I) or pharmaceutically acceptable salt thereof, and one or more excipients (also referred to as carriers and/or diluents in the pharmaceutical arts). The excipients are acceptable in the sense of being compatible with the other ingredients of the formulation and not deleterious to the recipient thereof (i.e., the patient).

Some embodiments further provide a process for the preparation of a pharmaceutical composition comprising combining, reacting, mixing (or admixing), etc. a compound of Formula (I) or salt thereof with at least one excipient.

The present compound may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

In one example, a liposome is used as the excipient to deliver the compound of Formula (I) or salt thereof. Preferably, the liposome is stable in the animal into which it has been administered for at least about 30 minutes, more preferably for at least about 1 hour, and even more preferably for at least about 24 hours. A liposome comprises a lipid composition that is capable of targeting the compound of Formula (I) to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Suitable liposomes for use in the present invention include those liposomes standardly used in, for example, in drug delivery methods known to those of skill in the art. Optionally, a liposome comprises a compound capable of targeting the liposome to a particular cell type, such as a cell-specific ligand exposed on the outer surface of the liposome. Complexing a liposome with the compound of Formula (I) can be achieved using methods which are standard in the art.

In a specific embodiment, the compound of Formula (I) may incorporate itself into the wall of the liposome. The core of the liposome may include a second compound, for example, a second anticancer drug to be used in combination with the compound of Formula (I). The liposome may be constructed to comprise both the compound of Formula (I) and the second desired compound. The liposome may also be modified as desired for targeted drug delivery of the compound of Formula (I), the second compound, or both. In one embodiment, targeted delivery of the compound of Formula (I) or the second compound (if present) may result in increased efficacy and less side effects relative to untargeted delivery mechanisms.

Pharmaceutical compositions may be in unit dose form containing a predetermined amount of active ingredient per unit dose. Such a unit may contain a therapeutically effective dose of the FAS inhibiting compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The FAS inhibiting compound, salt thereof, or the pharmaceutical composition may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules may be prepared by comminuting the FAS inhibiting compound to a suitable fine size and mixing with a similarly comminuted pharmaceutical carrier such as an edible carbohydrate, as, for example, starch or mannitol. Flavoring, preservative, dispersing, and coloring agents can also be present.

Capsules may be made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets may be formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs may be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation may also be prepared to prolong or sustain the release as, for example, by coating or embedding particulate material in polymers, wax, or the like.

The term "treatment," as it applies to a human, veterinary, or research subject, refers to therapeutic treatment, prophylactic or preventative measures, to research and diagnostic applications. As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a method of treatment in a mammal, especially a human, suffering from disease conditions targeted by the present FAS inhibiting compounds. Such treatment comprises the step of administering a therapeutically effective amount of a compound of Formula (I) or salt thereof to said mammal, particularly a human. Treatment can also comprise the step of administering a therapeutically effective amount of a pharmaceutical composition containing a compound of Formula (I) or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

As used herein, the term "therapeutically effective amount" is an amount sufficient to treat a specified disorder or disease or alternatively to obtain a pharmacological response treating a disorder or disease. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a FAS inhibiting compound of Formula (I), as well as salts thereof, may be administered as the raw chemical. Additionally, the active ingredient may be presented as a pharmaceutical composition.

While it is possible that, for use in therapy, that a therapeutically effective amount of a FAS inhibiting compound of Formula (I) or salt thereof may be administered as the raw chemical, it is typically presented as the active ingredient of a pharmaceutical composition or formulation.

The precise therapeutically effective amount of a compound or salt thereof of the present disclosure will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a FAS inhibiting compound of Formula (I) or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the FAS inhibiting compound of Formula (I) per se. Similar dosages should be appropriate for treatment (including prophylaxis) of the other conditions referred herein for treatment. In general, determination of appropriate dosing can be readily arrived at by one skilled in medicine or the pharmacy art.

Kits

The present disclosure also provides for a kit comprising the present compound/composition. The kit may be for use in the treatment or prophylaxis of cancer or other conditions. Kits according to the invention include package(s) (e.g., vessels) comprising the present compounds or compositions. The present compounds may be present in the pharmaceutical compositions as described herein. The present compounds may be present in unit dosage forms.

Examples of pharmaceutical packaging materials include, but are not limited to, bottles, tubes, inhalers, pumps, bags, vials, containers, syringes, bottles, and any packaging material suitable for a selected formulation and intended mode of administration and treatment.

Kits can contain instructions for administering the present compounds or compositions to a patient. Kits also can comprise instructions for uses of the present compounds or compositions. Kits also can contain labeling or product inserts for the present compounds or compositions. The kits also can include buffers for preparing solutions for conducting the methods. The instruction of the kits may state that the present compounds or compositions are to be used to treat, or treat prophylactically, cancer or related conditions.

Subjects, which may be treated according to the present disclosure include all animals which may benefit from administration of the present compounds or compositions. Such subjects include mammals, preferably humans, but can also be an animal such as dogs and cats, farm animals such as cows, pigs, sheep, horses, goats and the like, and laboratory animals (e.g., rats, mice, guinea pigs, and the like).

EXAMPLES

The present disclosure can be better understood by reference to the following examples which are offered by way of illustration. The present disclosure is not limited to the examples given herein. The derivatives described herein were prepared by the general methods described below. Formulas and R group designations used in the schemes below are meant to be used for this section only, and they may be inconsistent with those in the claims.

Example 1

The synthesis of the FAS inhibiting compounds illustrated above as Formulae II, III, IV and V is described as follows:

1) 2-Hydroxyethyl3-(5-bromo-2,4-dioxo-3,4-dihydropirimidin-1(2H)-yl)propanoate:

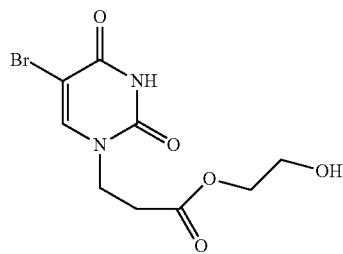 [SMILES: O=C(CCn1cc(Br)c(=O)[nH]c1=O)OCCO]

To a round-bottomed flask 5-Bromouracil (1.0 mmol) and 10 ml of acetonitrile were added. To this mixture triethylamine (1.0 mmol) was added and it was stirred for 5 minutes, followed by drop wise addition of (2-hydroxyethyl) acrylate (HEA) while stirring. The mixture was heated and kept at temperature of 60° C. for 2.5 hours. Afterwards, next portion of (2-hydroxyethyl) acrylate (0.6 mmol) was added and the heating was continued for the next 8-10 hours. Reaction was monitored by TLC. Upon completion of reaction, the solvent was evaporated under reduced pressure. Crude crystals were macerated with ethyl acetate, filtered off, dried on air and recrystallized from mixture of ethanol and ethyl acetate.

2) 3-(3,4-Dihydro-5-bromo-2,4-dioxopyrimidin-1(2H)-yl)propanoic acid:

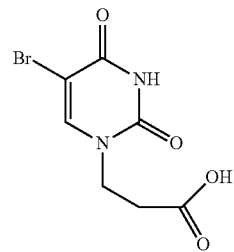 [SMILES: O=C(O)CCn1cc(Br)c(=O)[nH]c1=O]

The above Michael-type adduct of uracil to HEA (1 mmol) was refluxed in 5% $HCl_{aq}$ (8 ml). During first 5 minutes of refluxing solid phase disappeared. During the next 15 minutes of boiling neo-crystalline material appeared. The mixture was then cooled to room temperature, which resulted in further precipitation of fine-formed crystals. The post-reaction mixture was kept for 16 h in refrigerator. Afterwards crystals were filtered off and rinsed with ice-water to neutral pH.

3) Hexadecyl 3-(5-bromo-2,4-dioxo-3,4-dihydropyrimidin-1(2H)-yl)propanoate:

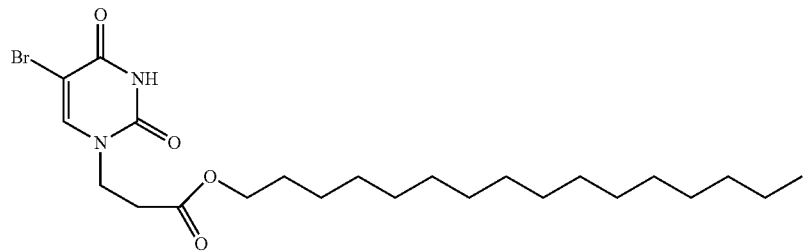 [SMILES: CCCCCCCCCCCCCCCCOC(=O)CCn1cc(Br)c(=O)[nH]c1=O]

The above acid of uracil (1.0 mmol) was added to a round bottom flask in 10 ml of dry THF. To this solution DCC (1.1 mmol) was added and reaction mixture was stirred for 10 minutes. After this, hexadecanol (1.1 mmol) was added to the reaction mixture and reaction was stirred overnight at room temperature. The insoluble N,N'-dicyclohexylurea was filtered off and solvent from the filtrate was evaporated under reduced pressure. Remaining solid crude was purified by 2% $CH_3CN$/Hexanes solvent system to give pure Compound 1A in 80% yield.

Example 2

Figure 1:
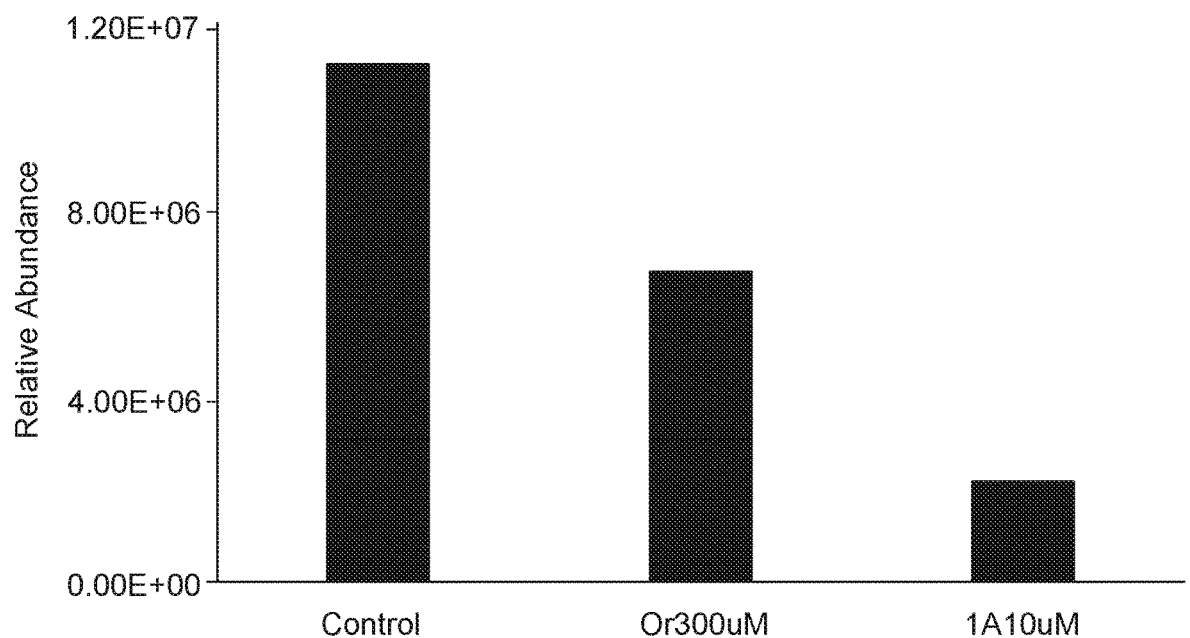
FIG. 1 illustrates a mass spectrometry analysis for the de novo synthesis of $^{13}C$-labeled palmitate in the presence of the FAS inhibitor, Compound 1A (hexadecyl 3-(5-bromo-2,4-dioxo-3,4-dihydropyrimidin-1(2H)-yl)propanoate) at the concentration of 10 μM. Control: vehicle (DMSO, dimethyl sulfoxide) as a control; "Or300 μM": ORLISTAT® at the concentration of 300 μM.

Mass spectrometry was performed to measure the de novo production of $^{13}C$-labeled palmitate. The FAS inhibiting compounds of Formulae II, III, IV and V (e.g., Compound 1A) were compared with ORLISTAT® and a control. The results are illustrated in FIG. 1.

Identification and quantification of palmitic acid ion was performed by a high resolution accurate mass instrument (the Q-Exactive Orbitrap) using samples extracted from cells with Folch buffer and separated by liquid chromatography described here; a high performance liquid chromatography C18 Polar Ascentis Express column (Supelco, 2.1×150 mm; 2.7 μm) separated small molecules were analyzed with the Q-Exactive in positive ion mode at 70,000 resolution (Full MS mode) followed by product scan at 35,000 resolution. Positive ion mode parameters were optimized for the ionization of the palmitic acid ion. Qual Browser program was used to manually integrate the signal areas from the palmitic ion molecules.

Data was averaged from three samples per group and corrected for protein content of the cells. The palmitic acid ion area was determined as the area under the curve of signal intensity in the integrated precursor extracted ion chromatogram. Ratio of C13 ion to C12 ion was considered for area calculations.

Example 3

Figure 2:
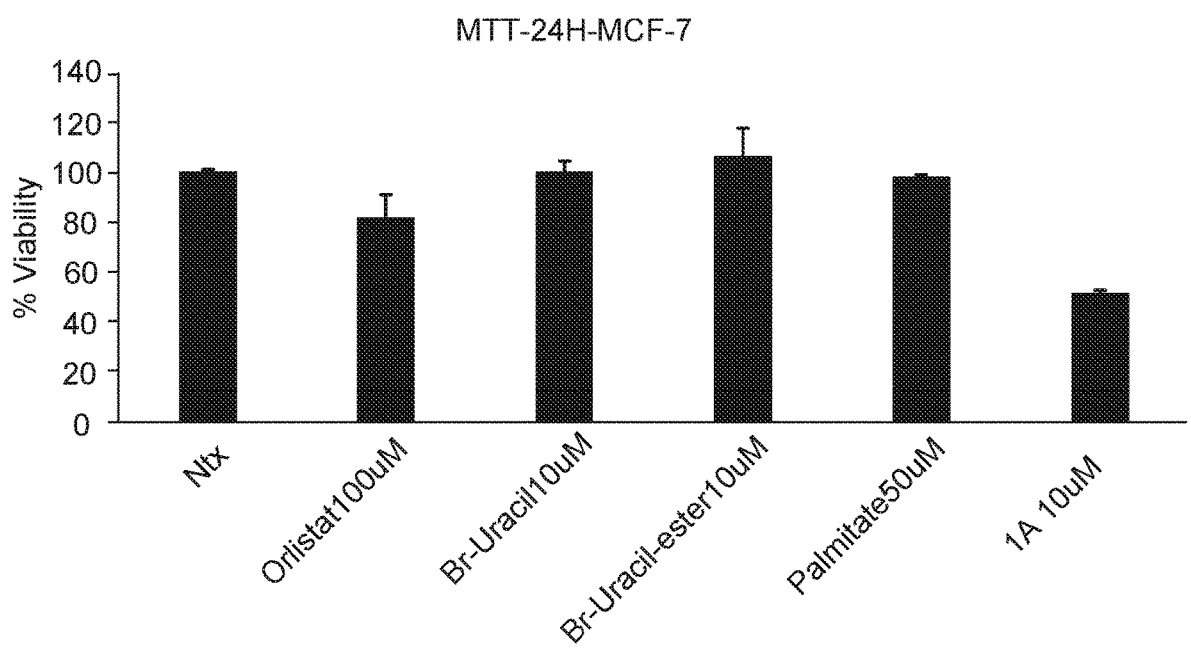
FIG. 2 illustrates MTT assay results showing cell viability for MCF-7 breast cancer cells treated with the FAS inhibitor, Compound 1A, at the concentration of 10 μM, for 24 hours ("1A10 μM"). MCF-7 cells were also treated with 100 μM ORLISTAT® ("Orlistat100 μM"), 10 μM Br-Uracil ("Br-Uracil10 μM"), 10 μM Br-Uracil-ester ("Br-Uracil-ester10 μM"), 50 μM palmitate ("Palmitate50 μM"), and vehicle as a control ("Ntx").

An MTT assay was performed with the FAS inhibiting compounds of Formulae II, III, IV and V (e.g., Compound 1A) on MCF-7 breast cancer cells, with an IC50 of about 10 M after 24 hours of treatment. The results are illustrated in FIG. 2.

Antiproliferative effect of FAS inhibitors on MCF-7 cells was determined by performing MTT assay. Roughly, 10,000 cells per well were plated in 96-well cell culture microplate (Costar, USA) and incubated overnight in full media (DMEM containing 10% FBS) for cells to adhere to the plate. Cells were then treated with various concentrations of inhibitors and vehicle for 24 hrs in serum free media. Cell viability was evaluated by the MTT (Sigma-Aldrich, St. Louis, Mont.) assay. The absorbance of solubilized formazan was read at 570 nm using ELISA reader (Bio-TEK, Synergy-1).

Example 4

Figure 3:
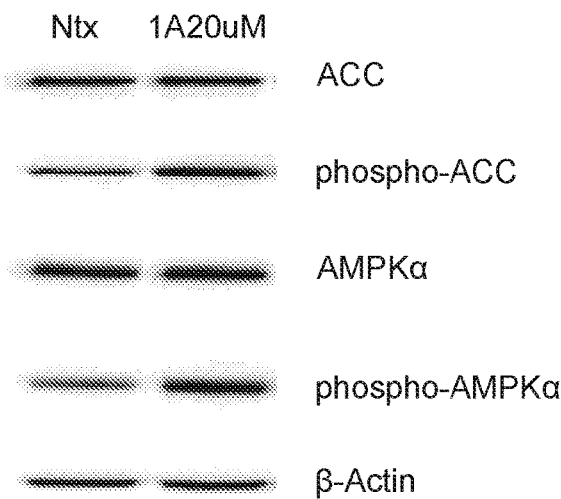
FIG. 3 illustrates an immunoblot analyzing the levels of fatty acid synthase (FAS, or FASN) and the other proteins when MCF-7 cells were treated with the FAS inhibitor, Compound 1A, at the concentration of 20 μM, for 24 hours.

Immunoblots were prepared with the FAS inhibiting compounds of Formulae II, III, IV and V (e.g., Compound 1A). Regulation of FAS, acetyl-CoA carboxylase ("ACC"), phosphorylated ACC ("pACC"), adenosine monophosphate-activated protein kinase ("AMPKα"), and phosphorylated AMPKα("pAMPKα") proteins were measured and compared with the control β-actin. The results are illustrated in FIG. 3.

After specific treatments, cells were harvested and lysed on ice for 30 min in lysis buffer containing 150 mM NaCl, 100 mM Tris (pH 8.0), 1% Triton X-100, 1% deoxycholic acid, 0.1% SDS, 5 mM EDTA, 10 mM sodium formate, 1 mM sodium orthovanadate, 2 mM leupeptin, 2 mM aprotinin, 1 mM phenylmethylsulfonyl fluoride, 1 mM dithiothreitol, and 2 mM pepstatin A. After centrifugation at 14,000 g for 15 min at 4° C., the supernatant was collected as the total cellular protein extract. The protein concentrations were determined using a bicinchoninic acid protein assay kit (Pierce Biotechnology, Rockford, Ill.). Equal amount of proteins per sample (30 μg) were resolved on a 10% sodium dodecyl sulfate-polyacrylamide gel by electrophoresis (SDS-PAGE) and transferred onto a nitrocellulose membrane. The membrane was blocked with T-PBS (0.3% Tween-20 in PBS) containing 5% dry milk and incubated with primary antibody overnight at 4° C. After three washes with T-PBS, the membrane was incubated with HRP-conjugated secondary antibody for 2 hrs at room temperature and then washed with 0.05% Tween-20 in PBS. Immunoreactive proteins were detected by chemiluminescence (Supersignal West Femto; Pierce, Rockford, Ill.) and quantified by imaging densitometry using UN-SCAN-IT digitizing software (Silk Scientific, Orem, Utah).

Example 5

We treated H460 lung cancer cells, MDA-MB-231 breast cancer cells, and PC-3 prostate cancer cells with the FAS inhibitor, Compound 1A. MTT assays clearly indicated that 5-Bromouracil, 5-Bromouracil ester (which is the product of the first reaction in Example 1), and palmitate (carbon chain alone without the 5-Bromouracil ester) alone showed no anticancer effect on these cells.

Compound 1A significantly reduced the viability of H460 and MDA-MB-231 cells after a 24-hr treatment (FIGS. 4 and 5), and reduced the viability of PC-3 cells after a 72-hr treatment (FIG. 6B).

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A compound of Formula (I):

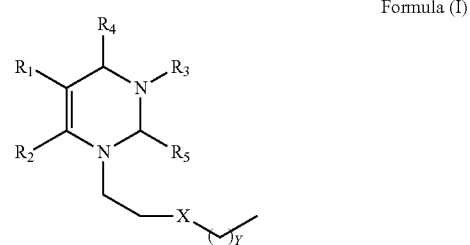

Formula (I)

or a pharmaceutically acceptable salt thereof, wherein $R_1$ is bromine; wherein each of $R_2$ and $R_3$ is hydrogen; wherein each of $R_4$ and $R_5$ is carbonyl; wherein X is ester; and wherein Y is between 4 and 20.

2. A pharmaceutical composition comprising a compound of Formula (I):

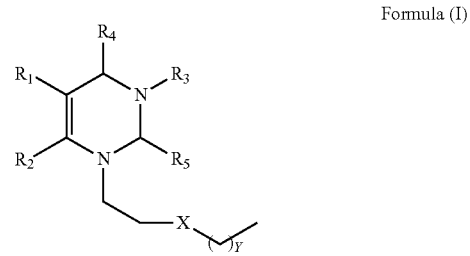

Formula (I)

or a pharmaceutically acceptable salt thereof, and a pharmaceutically acceptable carrier, wherein $R_1$ is selected from hydrogen, alkyl, alkenyl, alkynyl, aromatic, heterocyclic, halogen, hydroxyl, carbonyl, aldehyde, carboxylic acid, ester, ether, amide, amino, nitro, nitrile, thiol, and sulfonic acid; wherein each of $R_2$ and $R_3$ is hydrogen, wherein each of $R_4$ and $R_5$ is carbonyl, wherein X is ester; and wherein Y is between 2 and 20.

3. The pharmaceutical composition of claim 2, wherein the pharmaceutically acceptable carrier is a liposome.

4. A compound represented by Formula (II):

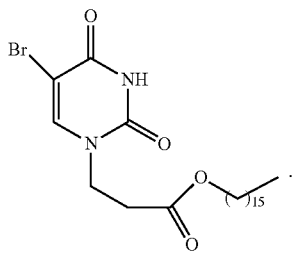

Formula (II)

5. A pharmaceutical composition comprising the compound of claim 4 and a pharmaceutically acceptable carrier.

6. The pharmaceutical composition of claim 5, wherein the pharmaceutically acceptable carrier is a liposome.

7. A compound of Formula (I):

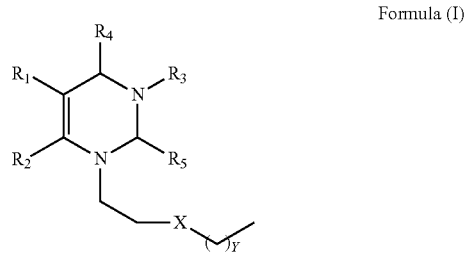

Formula (I)

or a pharmaceutically acceptable salt thereof, wherein $R_1$ is halogen, wherein each of $R_2$ and $R_3$ is hydrogen, wherein each of $R_4$ and $R_5$ is carbonyl; wherein X is ester; and wherein Y is between 4 and 20.

* * * * *